(12) United States Patent
Kim et al.

(10) Patent No.: US 11,650,203 B2
(45) Date of Patent: May 16, 2023

(54) ONE-POT BIOSENSOR AND IMMUNOASSAY METHOD USING THE SAME

(71) Applicant: GIST (Gwangju Institute of Science and Technology), Gwangju (KR)

(72) Inventors: Min Gon Kim, Gwangju (KR); Ki Hyeun Kim, Gwangju (KR); Eun Jung Jo, Gwangju (KR); Dong Gu Hong, Gwangju (KR)

(73) Assignee: GIST (Gwangju Institute of Science and Technology), Gwangju (KR)

( * ) Notice: Subject to any disclaimer, the term of this patent is extended or adjusted under 35 U.S.C. 154(b) by 197 days.

(21) Appl. No.: 17/361,660

(22) Filed: Jun. 29, 2021

(65) Prior Publication Data
US 2021/0405042 A1    Dec. 30, 2021

(30) Foreign Application Priority Data
Jun. 30, 2020    (KR) .......................... 10-2020-0080376

(51) Int. Cl.
*G01N 33/543* (2006.01)
*G01N 21/64* (2006.01)
*G01N 33/538* (2006.01)

(52) U.S. Cl.
CPC ....... *G01N 33/54366* (2013.01); *G01N 21/64* (2013.01); *G01N 33/538* (2013.01)

(58) Field of Classification Search
None
See application file for complete search history.

(56) References Cited

U.S. PATENT DOCUMENTS

| 9,630,172 B2* | 4/2017 | Kim | B01J 35/023 |
| 2016/0107152 A1* | 4/2016 | Tseng | B01J 23/14 |
| | | | 502/343 |

FOREIGN PATENT DOCUMENTS

| KR | 10-2013-0106044 A | 9/2013 |
| KR | 10-2015-0055925 A | 5/2015 |

OTHER PUBLICATIONS

Kihyeun Kim et al., Solid-Phase Photocatalysts: Physical Vapor Desposition of Au Nanoislands on Porous TiO2 Films tor Millimolar H2O2 Production within a Few Minutes; ACS Catal 2019, 9, 9206-9211.

(Continued)

*Primary Examiner* — Rebecca M Giere
(74) *Attorney, Agent, or Firm* — Studebaker & Brackett PC

(57) ABSTRACT

Disclosed are a one-pot biosensor and an immunoassay method using the same. The one-pot biosensor includes a photocatalyst substrate deposited with metal nanoparticles; and a reaction pad which is disposed on an upper surface of the photocatalyst substrate and includes a first binding material-fluorescent material complex specifically binding to a molecule to be detected, and the immunoassay method using the same. The one-pot biosensor may detect a target by once solution injection and has a size enough to be portable. Accordingly, since the one-pot biosensor can detect the target by only once solution injection without a washing step, because of a sensor platform capable of being easily used by an individual other than a diagnostic expert, it is predicted to be positioned as a means capable of confirming the health condition of the individual without seeing the doctor, such as a pregnancy diagnostic kit which has been currently commercialized.

19 Claims, 3 Drawing Sheets

(56) References Cited

OTHER PUBLICATIONS

Al-Ogaidi et al. "Detection of the ovarian cancer biomarker CA-125 using chemiluminescence resonance energy transfer to graphene quantum dots", Chemical Communications, 2014, vol. 50, Nov. 28, 2013, pp. 1344-1346, The Royal Society of Chemistry.
Liu et al., "Efficient Hydrogen Peroxide Generation Utilizing Photocatalytic Oxygen Reduction at a Triphase Interface", Science, vol. 17, Jul. 26, 2019, pp. 67-73.
An Office Action mailed by the Korean Intellectual Property Office dated Apr. 22, 2022, which corresponds to Korean Patent Application No. 10-2020-0080376 and is related to U.S. Appl. No. 17/361,660.
A Notice of Allowance mailed by the Korean Intellectual Property Office dated Oct. 12, 2022, which corresponds to Korean Patent Application No. 10-2020-0080376 and is related to U.S. Appl. No. 17/361,660.

\* cited by examiner

ONE-POT BIOSENSOR AND IMMUNOASSAY METHOD USING THE SAME

CROSS-REFERENCE TO RELATED APPLICATIONS

This application claims the priority of Korean Patent Application No. 10-2020-0080376 filed on Jun. 30, 2020, in the Korean Intellectual Property Office, the disclosure of which is incorporated herein by reference.

BACKGROUND OF THE INVENTION

Field of the Invention

The present disclosure relates to a one-pot biosensor and an immunoassay method using the same, and more particularly, to a one-pot biosensor which includes a photocatalyst substrate (110) deposited with metal nanoparticles; and a reaction pad (10) which is disposed on an upper surface of the photocatalyst substrate and includes a first binding material-fluorescent material complex specifically binding to a molecule to be detected, and an immunoassay method using the same.

Description of the Related Art

A biosensor is a system or apparatus for detecting an analyte in which a physicochemical detector component and a sensitive biological component are combined. Components of a typical biosensor system include a biological element, a converter or detector element, and a related electronic or signal processor, which represent test results in a critical and useful manner. The biological element includes a biological material, such as tissues, microorganisms, organs, cell receptors, enzymes, antibodies, nucleic acids, etc., which may be generated by typically known biological processing processes.

Development of a point-of-care biosensor is important in terms of improvement of the quality of personal life and social cost problems. When an individual can directly perform immediate and continuous diagnosis by using the point-of-care sensor, it is possible not only to increase the survival rate, but also to enable the health management to reduce a progression rate by early diagnosing incurable diseases such as dementia.

However, the current diagnostic technology needs to be performed by experts because the process thereof is complicated and tools or equipment are required. Therefore, there is a need for a biosensor of a simple operation method that may be directly used by individuals, and problems to be solved are greatly 1) to be detected by once solution injection (including a target), and 2) to be portable.

Fluorescence resonance energy transfer (FRET) means a phenomenon of moving energy between chromophores, which are molecules sensitive to light. The energy is transferred to a recipient chromophore by dipole-dipole interaction when a donor chromophore is electronically in an excitation state. Since the efficiency of such energy transfer is inversely proportional to 106 of a distance between the donor and the recipient, the FRET changes very sensitively even in a slight distance change. The interaction between proteins may be examined by measuring the energy transfer efficiency between two types of fluorescent proteins (FPs) by using this principle. The basic concept of the FRET was found by Theodor Forster, the German scientist in 1948 to be called Forster resonance energy transfer, and even in this case, the abbreviation is FRET. Originally, only when two kinds of chromophores are fluorescent, it is called "fluorescence resonance energy transfer", but in the life sciences, since fluorescent proteins are mainly used in an experiment, it is generally referred to as fluorescence resonance energy transfer. Phosphorescent proteins instead of the fluorescent proteins are also used. The FRET is one of the most useful methods of observing protein-protein interactions in living cells as one of the life science research fields using fluorescent proteins.

The above-described technical configuration is the background art for helping in the understanding of the present invention, and does not mean a conventional technology widely known in the art to which the present invention pertains.

SUMMARY OF THE INVENTION

An object of the present disclosure is to provide a portable one-pot immune biosensor capable of detecting a target molecule by once sample solution injection.

An aspect of the present disclosure provides a one-pot biosensor including a photocatalyst substrate (110) deposited with metal nanoparticles; and a reaction pad (120) which is disposed on an upper surface of the photocatalyst substrate (110) and includes a first binding material-fluorescent material complex specifically binding to a molecule to be detected. Specifically, the biosensor is an immune sensor, and an immunoassay sensor.

The immunoassay sensor may refer to a device that is manufactured by combining a device that converts an electrochemical change, a thermal energy change, a fluorescence or color change, and the like shown in the reaction between the biological element and the material to be analyzed into a recognizable signal.

The expression "specifically binding" means specificity of a binding reagent, for example, an antibody, and may mean preferentially binding to a defined specimen or target material. In the presence of another potential target, it may be a feature of the binding to recognize the specific specimen or target material by the binding reagent or antibody. In some embodiments, a binding reagent that specifically binds to the specimen may avoid binding with other interference portion or portions in a sample to be tested.

The photocatalyst substrate 110 may generate peroxide when UV is irradiated, wherein the peroxide may be any one selected from the group consisting of hydrogen peroxide, carbamide peroxide, calcium peroxide, sodium percarbonate, sodium perborate, tetrasodiumpyrophosphate peroxidate, and mixtures thereof, but is not limited thereto.

Further, the photocatalyst substrate 110 may be deposited on the substrate with at least one material selected from the group consisting of titanium dioxide ($TiO_2$), zinc oxide (ZnO), porphyrin, carbon nitride ($C_3N_4$), tungsten oxide ($WO_3$), strontium titanate ($SrTiO_3$), sulfide cadmium (CdS), zirconium dioxide ($ZrO_2$), tin dioxide ($SnO_2$), niobium pentoxide, molybdenum diselenide ($MoSe_2$), and mixtures thereof, but is not limited thereto. The substrate may be any one of glass, plastic, metal, silicon, quartz, alumina substrates, but is not limited thereto.

The first binding material-fluorescent material complex is a first binding material-fluorescent material-nanoparticle complex in which the binding material and the fluorescent material are conjugated to the nanoparticle. The nanoparticle may be any one selected from the group consisting of metal nanoparticles, metal nanorods, quantum dot nanoparticles, magnetic nanoparticles, carbon nanoparticles, latex beads/ fluorescent nanoparticles, cellulose nanoparticles, and mixtures thereof, but is not limited thereto.

The shape of the nanoparticle of the present disclosure is not particularly limited, and the nanoparticle may be at least one selected from the group consisting of spherical particles, strawberry-like or sea urchin-like spherical particles of which various types of nanoparticles are placed on the surface, anisotropic particles, hollow particles, asymmetric particles, and angulated particles. The nanoparticle may have, for example, a nano sphere, a nano-rod, a nanocube, and a plurality of geometrical and non-geological shapes. In particular, in the case of the anisotropic particle or angulated particle such as a rod shape, a triangle, a prism, and a cube, a more reinforced signal may be provided as compared to the spherical particle in the ramen scattering. The shape and size of the nanoparticle may be appropriately controlled for maximizing surface plasmon. The manufacturing method of the various types of nanoparticles described above is known in a large number of documents.

The metal may be any one selected from the group consisting of Au, Ag, Pt, Pd, Al, Cu, Ni, Zn, Fe, Ti, Cu, Ni, Zn, Fe, Ti, Cr, Mo, and mixtures thereof, but any metal capable of being conjugated or bound with the first binding material and the fluorescent material may be used.

According to the prior paper (Kim et al., ACS Catal.2019, 9, 9206-9211.) published by the present inventors, it was confirmed that when a photocatalyst film is formed on a substrate and then the metal is deposited on the photocatalyst film by physical vapor deposition, the productivity of peroxide was increased up to 80 times as compared with a photocatalyst film which was not deposited with the metal. In addition, according to the prior paper, it was confirmed that Au generated the highest concentration of peroxide, and then the generation concentration of peroxide was decreased in order of Ag, Pt and Pd.

A sample buffer in which a detection sample is mixed may be injected into the reaction pad 120 including the first binding material-fluorescent material complex.

According to yet embodiment of the present disclosure, the biosensor may further include a sample pad 130, and in order to adjust the reaction rate, the sample buffer in which the detection sample is mixed may be injected through the sample pad 130 and the sample pad 130 may be connected or conjugated to the reaction pad 120.

The sample buffer may include a second binding material specifically binding to a molecule to be detected, an enzyme conjugated to the second binding material, and a fluorescent inhibitor.

The "specimen" is not particularly limited so long as containing a specimen to be detected (a molecule to be diagnosed). Illustratively, the sample may be a biological sample, for example, a biological fluid or a biological tissue. Examples of the biological fluid may include urine, blood (whole blood), plasma, serum, saliva, semen, stool, sputum, cerebrospinal fluid, tear, mucus, amniotic fluid, etc. The biological tissue is a cluster of cells, and may correspond to connective tissue, epithelial tissue, muscular tissue, neural tissue, etc., as a specific type of set with intracellular materials which typically form one of structural materials of human, animal, plant, bacteria, fungal or viral structures. In addition, examples of the biological tissue may also include organs, tumors, lymph nodes, arteries, and individual cells(s).

The enzyme may be any one selected from horseradish peroxidase, alkaline phosphatase, β-galactosidase, *Arthromyces ramosus* peroxidase, β-lactamase, glucose-6-phosphate dehydrogenase, urease, uricase, superoxide dismutase, luciferase, pyruvate kinase, lactate dehydrogenase, galactose oxidase, acetylcholine-sterase, enterokinase, tyrosinase, xanthine oxidase, and mixtures thereof, but is not limited thereto.

The enzyme may be conjugated or bind to the second binding material, and the second binding material and the enzyme may be conjugated or bind to each other by an antigen other than a target antigen-antibody pair, a complementary nucleotide chain pair, a pair of an aptamer and a target material, a peptide pair binding to each other, and a pair of avidin or streptavidin and biotin, but is not limited thereto.

The fluorescent inhibitor may be any one selected from the group consisting of a mixture of 4-aminoantipyrine and a compound selected from the group consisting of 4-chloro-1-naphthol, 2-naphthol, N,N-bis(4-sulfobutyl)-3,5dimethylaniline, N-ethyl-N-(2-hydroxy-3-sulfopropyl)-3-methoxyaniline, N-ethyl-N-(3-sulfopropyl)-3-methoxyaniline, N-ethyl-N-(3-sulfopropyl) aniline, N-ethyl-N-(2-hydroxy-3-sulfopropyl)-3,5dimethoxyaniline, N-(2-hydroxy-3-sulfopropyl)-3,5-dimethoxyaniline, N-ethyl-N-(2-hydroxy-3-sulfopropyl)-3,5dimethylaniline, N,N-bis(4-sulfobutyl)-3methylaniline, N-ethyl-N(2-hydroxy-3-sulfopropyl)-3-methylaniline, and N-ethyl-N-(3-sulfopropyl)-3-methylaniline, N-(4-aminobutyl)-N-ethylisoluminol, 3-amino-9-ethylcarbazole, N-(6-aminohexyl)-N-ethylisoluminol, 4-aminophthalhydrazide, 5-aminosalicylic acid, 2,2'-azino-bis(3-ethylbenzothiazoline-6sulfonic acid) (ABTS), 2,2'-azino-bis(3-ethylbenzothiazoline-6-sulfonic acid) diammonium, 4-chloro-7-nitrobenzofurazan, o-dianisidine, dicarboxidine dihydrochloride, guaiacol, iodonitrotetrazolium chloride, 3-(4,5-dimethylthiazol-2yl)-2,5-diphenyl-tetrazolium bromide formazan (MTT formazan), nitrotetrazolium blue chloride, o-phenylenediamine, 3,3',5,5'tetramethylbenzidine (TMB), tetrazolium violet, 2,3,5-triphenyltetrazolium chloride, 3,3'-diaminobenzidine tetrahydrochloride, 3,3'-diaminobenzidine (DAB), and mixtures thereof, but is not limited thereto.

The binding material may be selected from the group consisting of antibodies, antigens, nucleic acids, aptamers, hapten, antigen proteins, DNA, RNA binding proteins, cationic polymers, and mixtures thereof, and may use any material which binds specifically to a molecule to be detected.

The cationic polymer may be selected from the group consisting of chitosan, glycol chitosan, protamine, polylysine, polyarginine, polyamidoamine (PAMAM), polyethylenimine, dextran, hyaluronic acid, albumin, polymer polyethyleneimine (PEI), polyamine, polyvinyl amine (PVAM), and mixtures thereof.

The reaction pad 120 or the sample pad 130 may include a porous membrane which is any one selected from the group consisting of glass fiber, silica membrane, cellulose, nitrocellulose, cellulose acetate, cotton, nylon, and mixtures thereof, but is not limited thereto.

The fluorescent material may be any one selected from the group consisting of FAM, VIC, TET, JOE, HEX, CY3, CY5, ROX, RED610, TEXAS RED, RED670, and NED, but is not limited thereto.

Yet another embodiment of the present disclosure provides an immunoassay method using the one-pot biosensor.

The immunoassay method may include mixing a detection specimen and a sample buffer to inject the mixture into the reaction pad 120 of claim 1; irradiating UV to the sensor; and measuring a reduction change in fluorescence intensity.

The reduction change in the fluorescence intensity may be calculated by measuring the fluorescence intensity emitted from the fluorescent material immediately before the UV is irradiated and measuring the fluorescence intensity emitted from the fluorescent material after a predetermined time elapses after the UV is irradiated.

Further, when the biosensor includes the sample pad 130, the mixture of the detection specimen and the sample buffer may be injected through the sample pad 130.

In the irradiating of the UV, the UV irradiation time is preferably 10 to 30 seconds. The amount of peroxide generated at this time is 0.1 to 0.3 mM, and when the UV irradiation time is less than 10 seconds, the generated amount of peroxide is small and thus, a significant reduction change in the fluorescence intensity cannot be measured. In addition, when the UV irradiation time is more than 30 seconds, there is a disadvantage that a too large amount of peroxide is formed and the excess peroxide oxidizes a large amount of fluorescent inhibitor in the presence of horseradish peroxidase to reduce the fluorescence intensity even when the molecule to be detected is not present.

The measuring of the reduction change in the fluorescent intensity is preferably performed within 30 seconds to 5 minutes after the UV irradiation is terminated. At the time of less than 30 seconds, the precipitation of the oxidized fluorescent inhibitor is not properly performed, and thus, it is difficult to observe an FRET phenomenon. In the case of more than 5 minutes, the oxidized fluorescent inhibitor formed by an enzyme conjugated to the second binding material which does not bind to the molecule to be detected is precipitated and thus, the fluorescence intensity is reduced even when the molecule to be detected is not present, so that a significant result cannot be detected.

When simply describing the immunoassay method of the present disclosure, first, when the UV is irradiated to the photocatalyst substrate 110, peroxide is generated from the photocatalyst substrate 110 and the generated peroxide reacts with the enzyme conjugated with the second binding material to oxidize the fluorescent inhibitor.

The oxidized fluorescent inhibitor is precipitated to absorb an energy spectrum emitted by the fluorescent material around the fluorescent material of the first binding material-fluorescent material-nanoparticle complex (FRET phenomenon), and as a result, the fluorescence intensity of the fluorescent material is reduced.

As a first factor for generating such an FRET phenomenon, the energy spectrum absorbed by the oxidized fluorescent inhibitor needs to overlap with an energy spectrum emitted by the fluorescent material and a distance between the fluorescent material and the oxidized fluorescent inhibitor needs to be 10 nm or less.

When it is assumed that the first binding material and the second binding material are antibodies, the first binding material and the second binding material forma complex via an antigen which is a molecule to be detected. Generally, the size of the antibody is 10 nm and the enzyme conjugated to the second binding material is far away up to about 20 nm from the fluorescent material conjugated to the nanoparticle. Thereafter, the fluorescent inhibitor is oxidized by the peroxide generated in the photocatalyst substrate 110 and the enzyme conjugated to the second binding material.

Thereafter, when the oxidized fluorescent inhibitor is precipitated around the fluorescent material and a distance between the precipitated oxidized fluorescent inhibitor and the fluorescent material is 10 nm or less, the FRET phenomenon occurs and the fluorescence intensity emitted by a fluorescent dye is reduced. Accordingly, it is preferred to measure the reduction change of the fluorescence intensity after the predetermined time elapses after the UV irradiation.

The one-pot biosensor developed in the present disclosure may detect a target by once solution injection and has a size enough to be portable. Accordingly, since the one-pot biosensor can detect the target by only once solution injection without a washing step, because of a sensor platform capable of being easily used by an individual other than a diagnostic expert, it is predicted to be positioned as a means capable of confirming the health condition of the individual without seeing the doctor, such as a pregnancy diagnostic kit which has been currently commercialized.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Hereinafter, the present disclosure will be described in detail with reference to the accompanying drawings and embodiments. The drawings and embodiments are to illustrate a preferred embodiment of the present disclosure and serve to further understand the technical idea of the present disclosure together with the detailed description of the invention, and it is not interpreted that the scope of the present disclosure is not limited to the matters described in such drawings.

According to a specific embodiment, a one-pot biosensor of the present disclosure is configured in a form in which a paper membrane immobilized with a Cy5/capture antibody/gold nanorod complex is placed on an $Au/TiO_2$ photocatalyst film.

The corresponding one-pot immune sensor can detect a target (antigen) only by injecting components (HRP-conjugated detection antibody, chloronaphtol (CN), and IL-8 antigen) required for detecting the target at a time and irradiating UV. A driving principle is to induce the reduction of the fluorescence intensity of the fluorescent dye when the target is present and the reduction of the fluorescence intensity is shown by the FRET phenomenon.

More specifically, when the target is present, the HRP-conjugated detection antibody is attached to the Cy5/capture antibody/gold nanorod complex via the target and then UV is irradiated to generate hydrogen peroxide, and then the fluorescence of Cy5 is quenched by CN (precipitate) oxidized by HRP in the attached state.

At this time, the HRP present in the HRP-conjugated detection antibody which does not bind to the antigen does not contribute to the fluorescence quenching. The reason is that the FRET phenomenon inducing the fluorescence quenching occurs when the distance between the CN precipitate and Cy5 is 10 nm or less.

Figure 1:
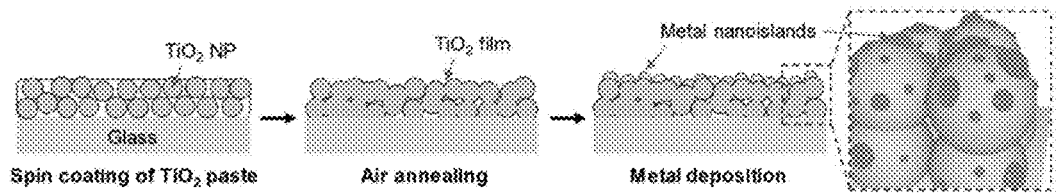
FIG. 1 is a schematic diagram of a manufacturing method of a photocatalyst substrate capable of generating hydrogen peroxide manufactured by spin coating and deposition processes in an embodiment of the present disclosure.

FIG. 1 is a schematic diagram schematically illustrating a manufacturing method of a photocatalyst substrate capable of generating hydrogen peroxide manufactured by spin coating and deposition processes in an embodiment of the present disclosure. The photocatalyst substrate used in the present disclosure may generate hydrogen peroxide at a high concentration of 1 mM when UV is irradiated.

The first binding material-fluorescent material complex or the first binding material-fluorescent material-metal nanoparticle complex of the present disclosure is not deposited together on the photocatalyst substrate, but is included in a separate reaction pad. According to the experiment of the present inventors, when the complex is immobilized together to the photocatalyst substrate, it was observed that the fluorescence disappeared immediately after the UV irradiation.

In a $H_2O_2$ generation principle of an $Au/TiO_2$ photocatalyst, reactive oxygen species are generated by UV and the generated reactive oxygen species react with each other to form $H_2O_2$. Generally, it has been known that the fluorescent materials are degraded by the reactive oxygen species, and the reason why the fluorescent characteristic disappears is that Cy5 is degraded before the generated reactive oxygen species become $H_2O_2$ by UV. Accordingly, according to the present disclosure, the first binding material-fluorescent material complex or the first binding material-fluorescent material-metal nanoparticle complex is included in the separate reaction pad. In this case, when the UV is irradiated, sufficient $H_2O_2$ is generated on the photocatalyst substrate and $H_2O_2$ generated on the photocatalyst substrate may be used for a detection reaction in the reaction pad.

Figure 2:
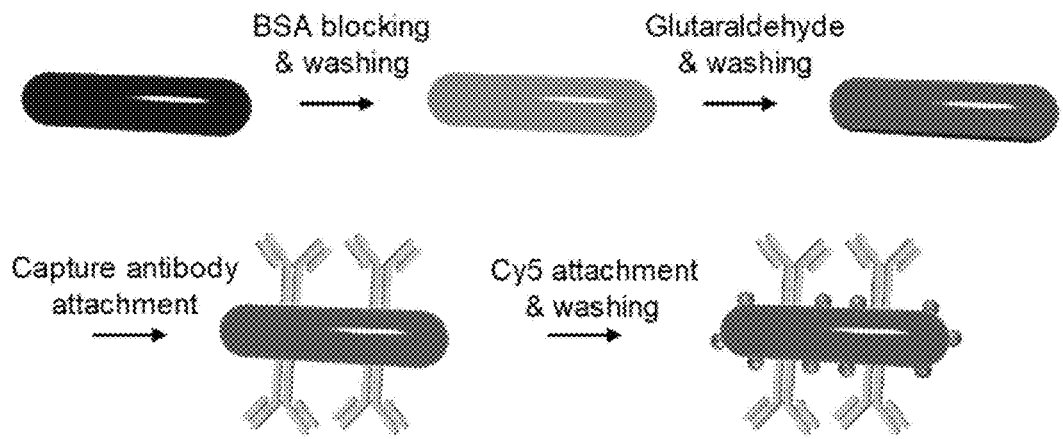
FIG. 2 illustrates a method of preparing an antibody-fluorescent dye-metal nanoparticle complex by attaching an antibody and Cy5 to a nanoparticle in an embodiment of the present disclosure.

FIG. 2 illustrates a method of preparing an antibody-fluorescent dye-metal nanoparticle complex by attaching an antibody and Cy5 to a nanoparticle according to an embodiment of the present disclosure.

First, bovine serum albumin (BSA) is attached to a gold nanorod and non-attached BSA was removed by a centrifuge. Thereafter, glutaldehyde binds to the BSA surface and non-attached glutaldehyde was removed by a centrifuge. A capture antibody and Cy5 are injected in sequence to attach the capture antibody and Cy5 to the glutaldehyde-BSA surface, and non-attached capture antibody and Cy5 were removed by a centrifuge. Finally, the glutaldehyde on the BSA surface which has been still activated by glycine is blocked to prepare a Cy5/capture antibody/gold nanorod complex.

Figure 3:
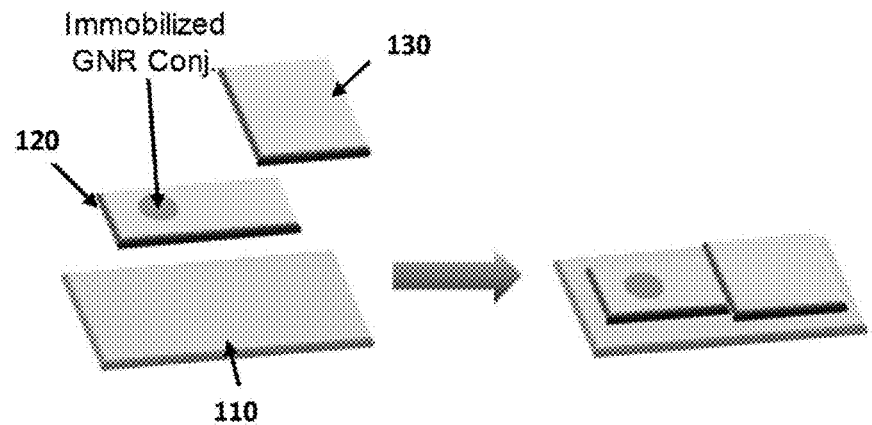
FIG. 3 is a diagram illustrating a manufacturing method of a one-pot biosensor in an embodiment of the present disclosure.

FIG. 3 illustrates a manufacturing process of the one-pot biosensor. First, 0.7 μL of a solution including the Cy5/capture antibody/gold nanorod complex was dropped to a single portion of the reaction pad 120 (paper membrane), and then dried to be immobilized to the membrane surface. Then, the reaction pad 120 is positioned on the $Au/TiO_2$ photocatalyst substrate 110 and the sample pad 130 is bound to an opposite end in which the Cy5/capture antibody/gold nanorod complex solution is not included to complete the one-pot biosensor. Here, the sample pad serves to continuously supply the solution because the solution capable of being generated in the target detecting process may be evaporated. Further, when the mixture of the specimen and the sample buffer is injected directly to the reaction pad, the reaction may rapidly occur and thus the detection efficiency may be deteriorated, so that the sample pad serves to adjust the supply rate of the specimen.

Figure 4:
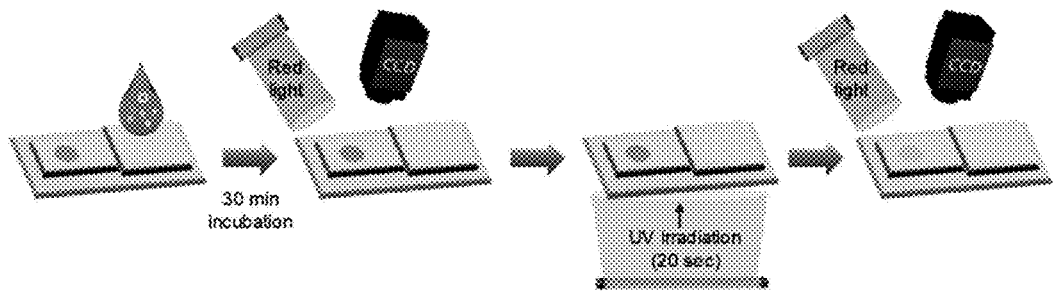
FIG. 4 illustrates a driving process of a one-pot biosensor of the present disclosure. In the driving process, first, a solution mixed with a biotinylated detection antibody, horseradish peroxidase (HRP)-labeled streptavidin, 4-chloro-1-naphthol, and an antigen is dropped on a paper membrane. Second, after 30 minutes, the fluorescence intensity of an antibody-fluorescent dye-metal nanoparticle complex is measured. Third, UV (365 nm) is irradiated for 20 seconds. Fourth, after 40 seconds, the fluorescence intensity of the antibody-fluorescent dye-metal nanoparticle complex is measured. A method of quantifying the target concentration is quantified by a change in the second measured fluorescence intensity and the first measured fluorescence intensity.
Figure 5:
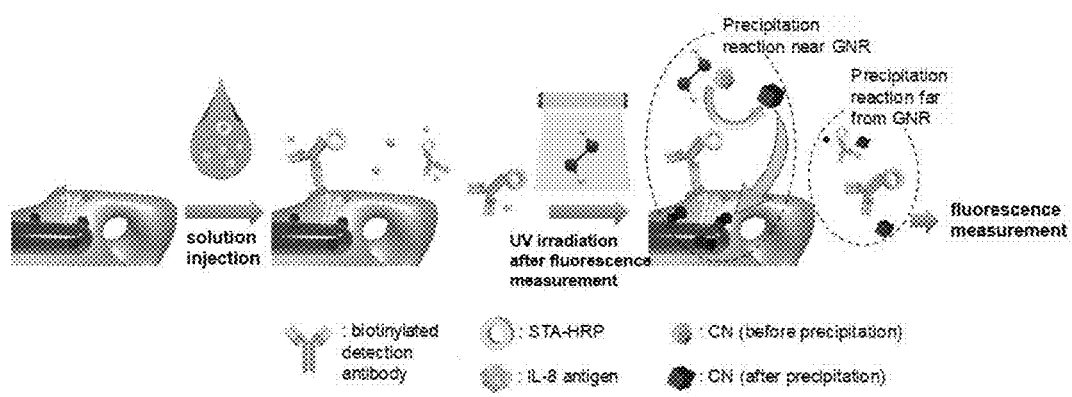
FIG. 5 illustrates a driving principle of a one-pot biosensor of the present disclosure. More specifically, after 30 minutes (time required for an immune reaction) of injecting a solution by a one-pot, the fluorescence intensity of the fluorescent dye may be quenched only by a 4-chloro-1-naphthol precipitate oxidized and formed by HRP immobilized to an antibody-fluorescent dye-metal nanoparticle complex by a target. At this time, the 4-chloro-1-naphthol precipitate formed by HRP which is not immobilized to the complex does almost not affect a change in fluorescence intensity of the fluorescent dye, and this reason is that a condition in which the fluorescent quenching phenomenon may occur appears only when a distance between the precipitate and the fluorescent dye is 10 nm or less, and this effect is based on Forster resonance energy transfer (FRET)

FIG. 4 illustrates a driving process of a one-pot biosensor of the present disclosure.

In the one-pot biosensor, the mixture of the specimen and the sample buffer was dropped to the sample pad 130 and reacted for 30 minutes, and then UV was irradiated for 20 seconds. The driving principle was based on the quenching of the fluorescent characteristic of Cy5 by the FRET phenomenon between Cy5 of the Cy5/capture antibody/gold nanorod complex and the oxidized CN (precipitate), and the oxidation reaction of CN occurs when HRP and hydrogen peroxide are present at the same time.

The FRET phenomenon occurs when the fluorescence spectrum of Cy5 and the absorption spectrum of oxidized CN overlap with each other while the distance between Cy5 and oxidized CN is 10 nm or less. FIG. 4 illustrates that the fluorescence spectrum of Cy5 and the absorption spectrum of oxidized CN overlap with each other.

In the one-pot biosensor of the present disclosure, it is more important to use that the FRET phenomenon occurs when the distance between Cy5 and oxidized CN is 10 nm or less, and this is because HRP immobilized to the Cy5/capture antibody/gold nanorod complex by the target and HRP floating simply in the solution serve to be distinguished. Since CN oxidized by HRP immobilized to the complex via the target is close to Cy5, the CN may contribute to fluorescence quenching of Cy5, but since CN oxidized by floating HRP which is not immobilized is far from Cy5 conjugated to the complex, it is difficult to induce the quenching of the fluorescence intensity. Therefore, when the FRET phenomenon occurring only at 10 nm or less is used, it is possible to implement a one-pot biosensor because only HRP immobilized by the antigen can be detected without removing floating HRP which is not immobilized.

When implementing the one-pot biosensor, it is additionally important that the oxidation reaction of CN needs to be performed after the antigen-antibody reaction ends (after 30 minutes). This is because only when the antigen-antibody reaction should occur, the immobilized HRP and the non-immobilized HRP may be distinguished in proportion to the antigen concentration.

Since the oxidation reaction of CN is performed when HRP and hydrogen peroxide are present at the same time, the one-pot biosensor of the present disclosure introduced the photocatalyst film capable of generating hydrogen peroxide. Accordingly, the one-pot biosensor was implemented based on the reduction of the fluorescence intensity by the FRET phenomenon between Cy5 and oxidized CN after the antigen-antibody reaction ends, and used a principle in which CN oxidized by the immobilized HRP mainly contributed to the FRET phenomenon.

Hereinafter, the present disclosure will be described in more detail through Examples. However, these Examples are just to help in the understanding of the present disclosure and the scope of the present disclosure is not limited to these Examples in any meaning.

EXAMPLES

1. Preparation of Photocatalyst Film

In order to prepare a photocatalyst film capable of generating hydrogen peroxide, paste including $TiO_2$ nanoparticles was spin-coated on a glass substrate (size: 15 mm×10 mm; width×length) and then heat-treated at 550° C. for 1 hour.

After a porous $TiO_2$ film was formed by heat treatment, gold (Au) was deposited by 5 nm by using an e-beam evaporator to form gold nanoislands and then completed the photocatalyst film capable of generating hydrogen peroxide.

2. Preparation of Antibody-Fluorescent Dye-Metal Nanoparticle Complex

In order to prepare an antibody-fluorescent dye-metal nanoparticle complex, first, bovine serum albumin was adsorbed on gold nanorods. Thereafter, the surface of the bovine serum albumin was activated using glutaldehyde and then unreacted glutaldehyde was removed by using a centrifuge.

Antibodies and Cy5 were injected in sequence to be attached to the bovine serum albumin and glycine was injected to inactivate the remaining glutaldehyde on the surface of the bovine serum albumin. Finally, the antibodies and Cy5 which did not participate in the complex formation were removed by a centrifuge to prepare the antibody-fluorescent dye-metal nanoparticle complex.

3. Manufacture of Biosensor

A solution including the antibody-fluorescent dye-metal nanoparticle complex prepared above was dropped on a porous paper membrane and then dried to physically adsorb the complex on the surface of the porous paper membrane. Thereafter, the paper membrane was placed on the photocatalyst film to complete the manufacture of the one-pot biosensor. Thereafter, the sample pad capable of injecting the sample was attached to the porous paper membrane including the complex.

<Experimental Example> IL-8 Detection Experiment

The performance of a one-pot immune sensor was tested by detecting IL-8 which was one of inflammatory biomarkers. An amount of a target IL-8 was quantified by a reduction change (quenching efficiency) of the fluorescence intensity. The quenching efficiency (%) is calculated by $[(I_{initial} - I_{final})/I_{initial}]*100$, wherein $I_{initial}$ represents the fluorescence intensity of fluorescent Cy5 before UV irradiation and $I_{final}$ represents the fluorescence intensity of the fluorescent Cy5 after UV irradiation.

Figure 6A:
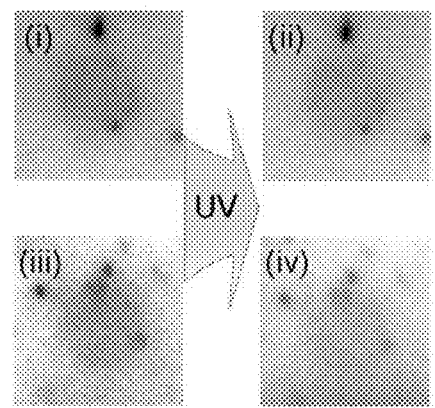
FIG. 6A illustrates fluorescent images before/after detecting a target (antigen), wherein (i) and (ii) illustrate images of Comparative group (antigen concentration: 0 ng/mL) and (iii) and (iv) illustrate images when the concentration of the antigen is 1 ng/mL.

FIG. 6A illustrates imaging of actual changes in fluorescence intensity according to presence or absence of antigen detection. It can be seen that (i) and (ii) illustrate that the fluorescence intensity is not almost reduced as Comparative Group (antigen concentration: 0 ng $mL^{-1}$), while when comparing (iii) and (iv), the fluorescence intensity of (iv) is reduced as compared to the fluorescence intensity of (iii).

Figure 6B:
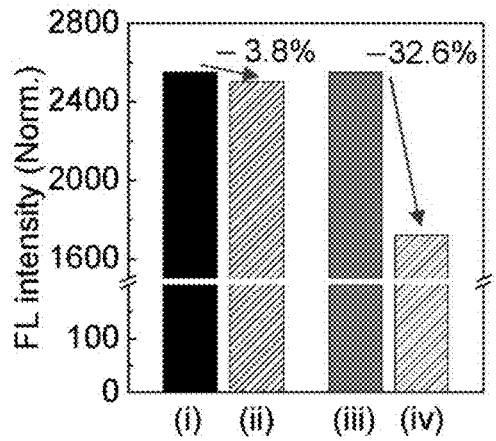
FIG. 6B illustrates quantification of the fluorescence intensities measured in FIG. 6A as a bar graph, wherein like FIG. 6A, (i) and (ii) illustrate fluorescence intensities of Comparative group (antigen concentration: 0 ng/mL) and (iii) and (iv) illustrate fluorescence intensities when the concentration of the antigen is 1 ng/mL. It is illustrated that the reduction degree of the fluorescence intensity varies depending on the presence or absence of the target.

FIG. 6B shows a graph illustrating reduction of the fluorescence intensity according to the presence or absence of IL-8. When there was no target, the quenching efficiency of 3.8% was observed, and when there was 1 ng/mL of the target, the quenching efficiency of 32.6% was observed.

Figure 7:
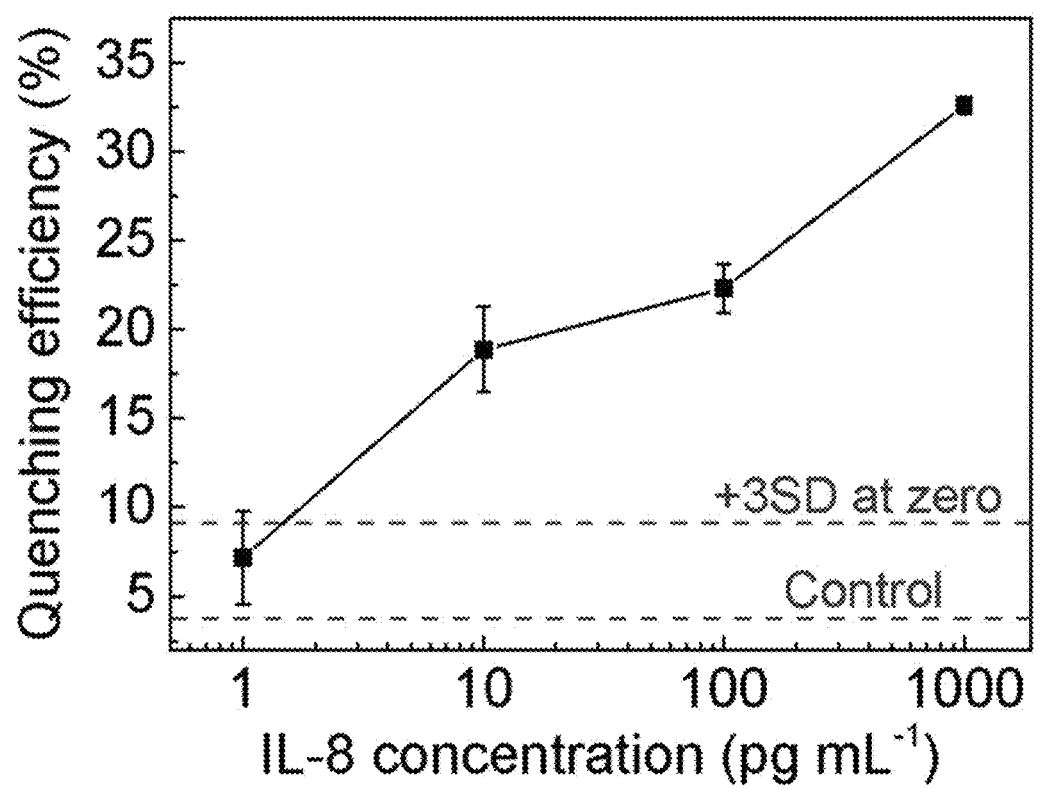
FIG. 7 illustrates numericization of a fluorescence quenching phenomenon of the fluorescent dye according to a target concentration. At this time, the quenching efficiency (%) is calculated by $[(I_{initial} - I_{final})/I_{initial}]*100$, wherein $I_{initial}$ represents the fluorescence intensity of the fluorescent dye before UV irradiation and $I_{final}$ represents the fluorescence intensity of the fluorescent dye after UV irradiation.

The increase in quenching efficiency was observed as the antigen (IL-8) concentration increased in the range of 0 to 1000 pg/ml (FIG. 7). A regression coefficient ($R^2$) for a linear curve was 0.967, and the slope and the intercept for a y-axis of the curve were 8.3710 and 7.3976, respectively. Each data point was obtained from average N=three separate measurements, and an error bar represented a standard deviation. The LOD (detection limit) was 0.92 pg/mL, which was calculated by [yLOD=yBlank+3.3×standard deviation of Blank].

The one-pot biosensor of the present disclosure was implemented by conjugating the photocatalyst film capable of generating hydrogen peroxide with the paper membrane immobilized with the Cy5/capture antibody/gold nanorod complex.

For the target detection, it was required only the process in which the solution was dropped once and after 30 minutes, UV was irradiated for 20 seconds, and the target concentration could be quantified by increasing the degree of fluorescence reduction of Cy5 in proportion to the increase in the target concentration.

The fluorescent reduction phenomenon occurred because the CN oxidized by the HRP immobilized to the Cy5/capture antibody/gold nanorod complex by the target mainly reduced the fluorescence of Cy5. This is because the FRET phenomenon, which is a medium of fluorescence reduction, is shown only at a short distance of 10 nm or less.

In addition, in order to oxidize CN after the time (30 minutes) required for the HRP immobilization by the target, hydrogen peroxide was produced by using the photocatalyst after 30 minutes to implement the one-pot biosensor.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A one-pot biosensor comprising:
   a photocatalyst substrate deposited with metal nanoparticles; and
   a reaction pad which is disposed on an upper surface of the photocatalyst substrate and includes a first binding material-fluorescent material complex specifically binding to a molecule to be detected.

2. The one-pot biosensor of claim 1, wherein the photocatalyst substrate generates peroxide by UV.

3. The one-pot biosensor of claim 2, wherein the peroxide is at least one selected from the group consisting of hydrogen peroxide, carbamide peroxide, calcium peroxide, sodium percarbonate, sodium perborate, tetrasodiumpyrophosphate peroxidate, and mixtures thereof.

4. The one-pot biosensor of claim 1, wherein the photocatalyst substrate is deposited with at least one material selected from the group consisting of titanium dioxide ($TiO_2$), zinc oxide (ZnO), porphyrin, carbon nitride ($C_3N_4$), tungsten oxide ($WO_3$), strontium titanate ($SrTiO_3$), sulfide cadmium (CdS), zirconium dioxide ($ZrO_2$), tin dioxide ($SnO_2$), niobium pentoxide, and molybdenum diselenide ($MoSe_2$).

5. The one-pot biosensor of claim 1, wherein in the complex, the binding material and the fluorescent material are conjugated to the nanoparticle.

6. The one-pot biosensor of claim 5, wherein the nanoparticles are at least one selected from the group consisting of metal nanoparticles, metal nanorods, quantum dot nanoparticles, magnetic nanoparticles, carbon nanoparticles, latex beads/fluorescent nanoparticles, and cellulose nanoparticles.

7. The one-pot biosensor of claim 6, wherein the metal is at least one selected from the group consisting of Au, Ag, Pt, Pd, Al, Cu, Ni, Zn, Fe, Ti, Cu, Ni, Zn, Fe, Ti, Cr, and Mo.

8. The one-pot biosensor of claim 1, wherein a sample buffer mixed with a detection specimen is injected to the reaction pad.

9. The one-pot biosensor of claim 8, wherein the sample buffer includes a second binding material specifically binding to a molecule to be detected, an enzyme conjugated to the second binding material, and a fluorescent inhibitor.

10. The one-pot biosensor of claim 9, wherein the enzyme is at least one selected from horseradish peroxidase, alkaline phosphatase, β-galactosidase, *Arthromyces ramosus* peroxidase, β-lactamase, glucose-6-phosphate dehydrogenase, urease, uricase, superoxide dismutase, luciferase, pyruvate kinase, lactate dehydrogenase, galactose oxidase, acetylcholine-sterase, enterokinase, tyrosinase, and xanthine oxidase.

11. The one-pot biosensor of claim 9, wherein the second binding material and the enzyme are conjugated to each other by an antigen other than a target antigen-antibody pair, a complementary nucleotide chain pair, a pair of an aptamer and a target material, a peptide pair binding to each other, and a pair of avidin or streptavidin and biotin.

12. The one-pot biosensor of claim 9, wherein the fluorescent inhibitor is any one selected from the group consisting of a mixture of 4-aminoantipyrine and a compound selected from the group consisting of 4-chloro-1-naphthol, 2-naphthol, N,N-bis(4-sulfobutyl)-3,5dimethylaniline, N-ethyl-N-(2-hydroxy-3-sulfopropyl)-3-methoxyaniline, N-ethyl-N-(3-sulfopropyl)-3-methoxyaniline, N-ethyl-N-(3-sulfopropyl)aniline, N-ethyl-N-(2-hydroxy-3-sulfopropyl)-3,5dimethoxyaniline, N-(2-hydroxy-3-sulfopropyl)-3,5-dimethoxyaniline, N-ethyl-N-(2-hydroxy-3-sulfopropyl)-3,5dimethylaniline, N,N-bis(4-sulfobutyl)-3methylaniline, N-ethyl-N(2-hydroxy-3-sulfopropyl)-3-methylaniline, and N-ethyl-N-(3-sulfopropyl)-3-methylaniline, N-(4-aminobutyl)-N-ethylisoluminol, 3-amino-9-ethylcarbazole, N-(6-aminohexyl)-N-ethylisoluminol, 4-aminophthalhydrazide, 5-aminosalicylic acid, 2,2'-azino-bis(3-ethylbenzothiazoline-6sulfonic acid) (ABTS), 2,2'-azino-bis(3-ethylbenzothiazoline-6-sulfonic acid) diammonium, 4-chloro-7-nitrobenzofurazan, o-dianisidine, dicarboxidine dihydrochloride, guaiacol, iodonitrotetrazolium chloride, 3-(4,5-dimethylthiazol-2yl)-2,5-diphenyl-tetrazolium bromide formazan (MTT formazan), nitrotetrazolium blue chloride, o-phenylenediamine, 3,3',5,5'tetramethylbenzidine (TMB), tetrazolium violet, 2,3,5-triphenyltetrazolium chloride, 3,3'-diaminobenzidine tetrahydrochloride, and 3,3'-diaminobenzidine (DAB).

13. The one-pot biosensor of claim 1, wherein the sensor further comprises a sample pad which is connected with the reaction pad and injected with a sample buffer mixed with a detection specimen.

14. The one-pot biosensor of claim 1, wherein the binding material is at least one selected from the group consisting of antibodies, antigens, nucleic acids, aptamers, hapten, antigen proteins, DNA, RNA binding proteins, and cationic polymers.

15. The one-pot biosensor of claim 1, wherein the pad includes a porous membrane which is any one selected from the group consisting of glass fiber, silica membrane, cellulose, nitrocellulose, cellulose acetate, cotton, and nylon.

16. The one-pot biosensor of claim 1, wherein the fluorescent material is any one selected from the group consisting of FAM, VIC, TET, JOE, HEX, CY3, CY5, ROX, RED610, TEXAS RED, RED670, and NED.

17. An immunoassay method using the biosensor according to claim 1 comprising the steps of:
    mixing a detection specimen and a sample buffer to inject the mixture to the reaction pad of claim 1;
    irradiating UV; and
    measuring a reduction change in fluorescence intensity.

18. The immunoassay method of claim 17, wherein the irradiating of the UV is performed for 10 to 30 seconds.

19. The immunoassay method of claim 17, wherein the measuring of the reduction change in the fluorescence intensity is performed within 30 seconds to 5 minutes after the UV irradiation is terminated.

* * * * *